US012151013B2

(12) United States Patent
Teboul

(10) Patent No.: US 12,151,013 B2
(45) Date of Patent: *Nov. 26, 2024

(54) METHODS OF DYEING KERATIN FIBERS WITH A PIGMENT DYEING COMPOSITION

(71) Applicant: L'OREAL, Paris (FR)

(72) Inventor: Karen Teboul, St. Mande (FR)

(73) Assignee: L'OREAL, Paris (FR)

( * ) Notice: Subject to any disclaimer, the term of this patent is extended or adjusted under 35 U.S.C. 154(b) by 90 days.

This patent is subject to a terminal disclaimer.

(21) Appl. No.: 17/389,917

(22) Filed: Jul. 30, 2021

(65) Prior Publication Data
US 2022/0079866 A1 Mar. 17, 2022

Related U.S. Application Data

(62) Division of application No. 14/367,370, filed as application No. PCT/EP2012/075421 on Dec. 13, 2012, now Pat. No. 11,376,208.

(60) Provisional application No. 61/593,027, filed on Jan. 31, 2012.

(30) Foreign Application Priority Data

Dec. 20, 2011 (FR) .................................. 1162003

(51) Int. Cl.
A61K 8/81 (2006.01)
A61K 8/895 (2006.01)
A61Q 1/10 (2006.01)
A61Q 5/06 (2006.01)

(52) U.S. Cl.
CPC ............ A61K 8/8147 (2013.01); A61K 8/895 (2013.01); A61Q 1/10 (2013.01); A61Q 5/065 (2013.01); A61K 2800/43 (2013.01); A61K 2800/48 (2013.01); A61K 2800/594 (2013.01)

(58) Field of Classification Search
CPC .................................................. A61Q 5/065
See application file for complete search history.

(56) References Cited

U.S. PATENT DOCUMENTS

| | | | |
|---|---|---|---|
| 2,463,611 A | 3/1949 | Green et al. |
| 3,175,993 A | 3/1965 | Weyenberg |
| 3,433,232 A | 3/1969 | Garrett |
| 3,599,647 A | 8/1971 | Fabbri |
| 4,578,266 A | 3/1986 | Tietjen et al. |
| 4,693,935 A | 9/1987 | Mazurek |
| 4,728,571 A | 3/1988 | Clemens et al. |
| 4,772,676 A | 9/1988 | Klosowski et al. |
| 4,871,827 A | 10/1989 | Klosowski et al. |
| 4,888,380 A | 12/1989 | Kamis et al. |
| 4,898,910 A | 2/1990 | Kamis et al. |
| 4,906,719 A | 3/1990 | Chu et al. |
| 4,962,174 A | 10/1990 | Bilgrien et al. |
| 4,972,037 A | 11/1990 | Garbe et al. |
| 5,059,414 A | 10/1991 | Dallal et al. |
| 5,162,410 A | 11/1992 | Sweet |
| 5,246,694 A | 9/1993 | Birthwistle |
| 5,645,609 A | 7/1997 | Andrean et al. |
| 5,799,669 A | 9/1998 | Briggs |
| 5,849,318 A | 12/1998 | Imai et al. |
| 5,874,069 A | 2/1999 | Mendolia et al. |
| 5,919,441 A | 7/1999 | Mendolia et al. |
| 5,948,393 A | 9/1999 | Tomomasa et al. |
| 5,961,665 A | 10/1999 | Fishman |
| 5,981,680 A | 11/1999 | Petroff et al. |
| 5,990,479 A | 11/1999 | Weiss et al. |
| 6,013,682 A | 1/2000 | Dalle et al. |
| 6,024,946 A | 2/2000 | Dubief et al. |
| 6,051,216 A | 4/2000 | Barr et al. |
| 6,106,577 A | 8/2000 | Audousset et al. |
| 6,225,198 B1 | 5/2001 | Alivisatos et al. |
| 6,606,943 B2 | 8/2003 | De Laforcade |
| 6,609,457 B1 | 8/2003 | De Laforcade |
| 7,026,424 B2 | 4/2006 | Schafer et al. |
| 7,351,405 B2 | 4/2008 | De La Poterie |
| 7,357,921 B2 | 4/2008 | Giroud |
| 7,503,939 B2 | 3/2009 | Umeno |
| 7,537,120 B1 | 5/2009 | Cardenas |
| 7,875,265 B2 | 1/2011 | Blin et al. |
| 7,942,937 B2 | 5/2011 | Brun |
| 8,105,393 B2 | 1/2012 | Suddaby et al. |

(Continued)

FOREIGN PATENT DOCUMENTS

| | | |
|---|---|---|
| CA | 711756 A | 6/1965 |
| CN | 101980690 A | 2/2011 |

(Continued)

OTHER PUBLICATIONS

Final Office Action for copending U.S. Appl. No. 14/367,376, mailed Dec. 18, 2019.
Non-Final Office Action for copending U.S. Appl. No. 14/367,376, mailed Aug. 15, 2019.
Notice of Allowance for copending U.S. Appl. No. 14/367,388, mailed Sep. 5, 2019.
Final Office Action for copending U.S. Appl. No. 14/367,388, mailed Apr. 2, 2019.
Non-Final Office Action for copending U.S. Appl. No. 14/411,679, mailed Apr. 5, 2019.

(Continued)

Primary Examiner — Gina C Justice
(74) Attorney, Agent, or Firm — THE MARBURY LAW GROUP PLLC

(57) ABSTRACT

The present invention relates to a composition for dyeing keratin fibres comprising at least one aqueous dispersion of particles of hybrid film-forming hydrophobic acrylic polymer, at least one linear block silicone copolymer and at least one pigment. It also relates to a dyeing method in which said composition is applied to the keratin fibres, the operation optionally being followed by a drying operation. The composition makes it possible to obtain a coloured, shampoo-resistant coating that leaves the treated fibres individualized, with an improved cosmetic feel.

20 Claims, No Drawings

(56) References Cited

U.S. PATENT DOCUMENTS

| | | |
|---|---|---|
| 8,124,914 B2 | 2/2012 | Yu |
| 8,137,413 B2 | 3/2012 | Wood et al. |
| 8,337,822 B2 | 12/2012 | Brun |
| 8,574,317 B2 | 11/2013 | Schmelz et al. |
| 10,744,080 B2 | 8/2020 | Teboul |
| 2002/0023555 A1 | 2/2002 | Laforcade |
| 2003/0175229 A1 | 9/2003 | Giroud |
| 2004/0120906 A1 | 6/2004 | Toumi et al. |
| 2004/0142831 A1 | 7/2004 | Jager Lezer |
| 2004/0180021 A1 | 9/2004 | De La Poterie |
| 2004/0182408 A1 | 9/2004 | Forcade |
| 2004/0210024 A1 | 10/2004 | Schafer et al. |
| 2004/0254325 A1 | 12/2004 | Kuepfer et al. |
| 2006/0085924 A1 | 4/2006 | Brun |
| 2006/0093568 A1 | 5/2006 | Blin et al. |
| 2006/0099164 A1 | 5/2006 | De La Poterie et al. |
| 2006/0115444 A1 | 6/2006 | Blin et al. |
| 2006/0116489 A1 | 6/2006 | Lennon |
| 2006/0127334 A1 | 6/2006 | Ferrari et al. |
| 2006/0134032 A1 | 6/2006 | Ilekti et al. |
| 2006/0134044 A1 | 6/2006 | Blin et al. |
| 2006/0134051 A1 | 6/2006 | Blin et al. |
| 2006/0147402 A1 | 7/2006 | Blin et al. |
| 2006/0147403 A1 | 7/2006 | Ferrari et al. |
| 2006/0216257 A1 | 9/2006 | Pays et al. |
| 2007/0044249 A1 | 3/2007 | Lisowski et al. |
| 2007/0224140 A1 | 9/2007 | Quadir et al. |
| 2008/0127429 A1 | 6/2008 | Brun et al. |
| 2008/0171010 A1 | 7/2008 | Brun |
| 2009/0151086 A1 | 6/2009 | Brun |
| 2009/0193595 A1 | 8/2009 | Brun et al. |
| 2009/0214458 A1 | 8/2009 | Brun et al. |
| 2010/0266517 A1 | 10/2010 | Dingley et al. |
| 2011/0005546 A1 | 1/2011 | Müller-Grünow et al. |
| 2011/0028571 A1 | 2/2011 | Hayakawa |
| 2011/0097289 A1 | 4/2011 | Viala et al. |
| 2011/0165104 A1 | 7/2011 | Molenda et al. |
| 2011/0300092 A1 | 12/2011 | Kambach et al. |
| 2013/0074864 A1 | 3/2013 | Nuzzo et al. |
| 2015/0007845 A1 | 1/2015 | Teboul |
| 2015/0125413 A1 | 5/2015 | Teboul |
| 2015/0132243 A1 | 5/2015 | Teboul |
| 2015/0164196 A1 | 6/2015 | Teboul et al. |
| 2015/0174041 A1 | 6/2015 | Teboul |
| 2015/0174051 A1 | 6/2015 | Teboul |
| 2015/0274972 A1 | 10/2015 | Mateu et al. |

FOREIGN PATENT DOCUMENTS

| | | | |
|---|---|---|---|
| CN | 102274134 A | | 12/2011 |
| EP | 0412704 A2 | | 2/1991 |
| EP | 0412707 A1 | | 2/1991 |
| EP | 0640105 A1 | | 3/1995 |
| EP | 0815836 A2 | | 1/1998 |
| EP | 0874017 A2 | | 10/1998 |
| EP | 1040873 A1 | | 10/2000 |
| EP | 1184426 A2 | | 3/2002 |
| EP | 1400234 A1 | | 3/2004 |
| EP | 1649898 A2 | | 4/2006 |
| EP | 2070516 A1 | | 6/2009 |
| EP | 2095810 A1 | | 9/2009 |
| FR | 2480096 A1 | | 10/1981 |
| FR | 2679771 A1 | | 2/1993 |
| FR | 2741530 A1 | | 5/1997 |
| FR | 2831430 A1 | | 5/2003 |
| FR | 2833489 A1 | | 6/2003 |
| FR | 2958189 A1 | | 10/2011 |
| GB | 2073672 A | | 10/1981 |
| JP | 05-017710 A | | 1/1993 |
| JP | 07-258460 A | | 10/1995 |
| JP | 09-188830 A | | 7/1997 |
| JP | 10-158450 A | | 6/1998 |
| JP | 10-158451 A | | 6/1998 |
| JP | 10-158541 A | | 6/1998 |
| JP | 2004-202251 A | | 7/2004 |
| JP | 2008-106067 A | | 5/2008 |
| JP | 2008-247761 A | | 10/2008 |
| JP | 2008-247879 A | | 10/2008 |
| JP | 2010-524917 A | | 7/2010 |
| JP | 2011-026263 A | | 2/2011 |
| WO | 92/21316 A1 | | 12/1992 |
| WO | 93/23446 A2 | | 11/1993 |
| WO | 95/00578 A1 | | 1/1995 |
| WO | 01/96450 A2 | | 12/2001 |
| WO | 03/014194 A1 | | 2/2003 |
| WO | 2004/028487 A2 | | 4/2004 |
| WO | 2008/142658 A2 | | 11/2008 |
| WO | 2010/071777 A1 | | 6/2010 |
| WO | 2013/092380 A1 | | 6/2013 |
| WO | 2013/092381 A1 | | 6/2013 |
| WO | 2013/092382 A1 | | 6/2013 |
| WO | 2013/092788 A1 | | 6/2013 |
| WO | 2014/001390 A1 | | 1/2014 |
| WO | 2014/001391 A1 | | 1/2014 |

OTHER PUBLICATIONS

Final Office Action for copending U.S. Appl. No. 14/411,671, mailed Apr. 19, 2019.
Final Office Action for copending U.S. Appl. No. 14/411,679, mailed Oct. 2, 2018.
Non-Final Office Action for copending U.S. Appl. No. 14/411,671, mailed Oct. 3, 2018.
Non-Final Office Action for copending U.S. Appl. No. 14/367,388, mailed Oct. 4, 2018.
Final Office Action for copending U.S. Appl. No. 14/367,376, mailed Dec. 21, 2018.
Moss et al., "Silicones as a Color-Lock Aid in Rinse-Off Hair Care Products," obtained online at: https://pdfs.semanticscholar.org/e78b/faa6983618b3b3896ad83c50e16a67513de.pdf (Year 2004).
Fang, K. et al., "New high molecular weight silicone polyether emulsions for use in personal care applications," IPCOM000200095D, Sep. 27, 2010.
Non-Final Office Action for copending U.S. Appl. No. 14/411,679, mailed Nov. 30, 2017.
Non-Final Office Action for copending U.S. Appl. No. 14/411,671, mailed Jun. 16, 2017.
Final Office Action for copending U.S. Appl. No. 14/411,671, mailed Apr. 6, 2018.
Chinese Office Action for counterpart Application No. 201380034576.3, mailed Feb. 5, 2018.
Machine translation of Notifications of Reasons for Refusal for counterpart Application No. JP2014-547862, mailed Nov. 10, 2016.
Office Action for counterpart Application EP12799223.8, mailed Jun. 1, 2017.
Final Office Action for copending U.S. Appl. No. 14/367,382, mailed Aug. 6, 2018.
International Search Report for PCT/EP2012/075421, (published as WO 2013/092381) dated Feb. 26, 2013.
International Search Report for PCT/EP2012/076269, (published as WO 2013/092788), dated Feb. 25, 2013.
International Search Report for PCT/EP2012/075419, (published as WO 2013/092380), dated May 8, 2013.
International Search Report for PCT/EP2012/075423, (published as WO 2013/092382), dated Feb. 28, 2013.
English language abstract for JP 5017710.
English language abstract for JP 7258460.
English language abstract for JP 9188830.
English language abstract for JP 10158541.
English language abstract for JP 10158450.
"Perfumes," Kirk-Othmer Encyclopedia of Chemical Technology, Fourth Edition, vol. 18, 1996, pp. 171-200.
Todd, Charles et al., "Volatile silicone fluids for cosmetic formulations," Cosmetics and Toiletries, Feb. 1990, vol. 105, pp. 53-64.
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.

(56) References Cited

OTHER PUBLICATIONS

Peng, Xiaogang et al., "Epitaxial Growth of Highly Luminescent CdSE/CdS Core/Shell Nanocrystals with Photostability and Electronic Accessibility," Journal of the American Chemical Society, vol. 119, No. 30, pp. 7019-7029.
ShinEtsu Unique Materials, ShinEtsu (revised 2010).
Final Office Action for copending U.S. Appl. No. 14/367,382, filed Nov. 25, 2016.
Non-Final Office Action for copending U.S. Appl. No. 14/367,376, filed Dec. 1, 2016.
Non-Final Office Action for copending U.S. Appl. No. 14/411,679, mailed Oct. 12, 2016.
Non-Final Office Action for copending U.S. Appl. No. 14/411,671, mailed Mar. 5, 2020.
Final Office Action for copending U.S. Appl. No. 14/411,671, mailed Oct. 13, 2020.
"Interpolymer luanches new polymers at in-cosmetics," Cosmetics Business, Apr. 8, 2011 (printed on Jul. 2, 2020 from https://www.cosmeticsbusiness.com/news/article_page/Interpolymer_launches_new_polymers_at_in-cosmetics/60339).
Notice of Allowance for copending U.S. Appl. No. 14/367,376, mailed Apr. 21, 2020.
Non-Final Office Action for copending U.S. Appl. No. 14/367,382, mailed Feb. 24, 2016.
Non-Final Office Action for copending U.S. Appl. No. 14/367,388, mailed Jan. 20, 2016.
Machine translation of Notification of Reasons for Refusal for counterpart Application JP2014-547862, dated Nov. 10, 2016.
Machine translation of Notification of Reasons for Refusal for counterpart Application JP2014-547861, dated Nov. 21, 2016.
Machine translation of Notification of Reasons for Refusal for counterpart Application JP2014-547863, dated Nov. 14, 2016.
Machine translation of First Office Action for counterpart Application CN 201380034562.1, dated Jan. 12, 2016.
Machine translation of Second Office Action for counterpart Application CN 201380034562.1, dated Nov. 30, 2016.
Machine translation of First Office Action for counterpart Application CN 201380034576.3, dated Dec. 31, 2015.
Machine translation of Second Office Action for counterpart Application CN 201380034576.3, dated Nov. 17, 2016.
Machine translation of Third Office Action for counterpart Application CN 201280062545, dated Apr. 10, 2017.
Final Office Action for U.S. Appl. No. 14/367,376, dated Jul. 3, 2017.
Non-Final Office Action for U.S. Appl. No. 14/367,382, dated Nov. 16, 2017.
Final Office Action for U.S. Appl. No. 14/367,388, dated Sep. 7, 2017.
Final Office Action for U.S. Appl. No. 14/367,370, dated Jun. 16, 2017.
International Search Report and Written Opinion for PCT/EP2013/063387, mailed Jan. 8, 2013.
International Search Report and Written Opinion for PCT/EP2013/063388, mailed Jan. 1, 2008.
Final Office Action for copending U.S. Appl. No. 14/411,671, dated Jun. 7, 2022.

METHODS OF DYEING KERATIN FIBERS WITH A PIGMENT DYEING COMPOSITION

CROSS REFERENCE TO RELATED APPLICATIONS

This is a divisional of U.S. application Ser. No. 14/367,370, filed Jun. 20, 2014, which is a national stage application of PCT/EP2012/075421, filed internationally on Dec. 13, 2012, which claims priority to U.S. Provisional Application No. 61/593,027, filed on Jan. 31, 2012, as well as French Application No. 1162003, filed on Dec. 20, 2011, all of which are incorporated by reference herein in their entireties.

The present invention relates to a composition for dyeing keratin fibres comprising an aqueous dispersion of particles of a particular acrylic polymer, a linear block silicone copolymer and a pigment, and also to a dyeing method using said composition.

It is already known practice in the field of dyeing keratin fibres, in particular human keratin fibres, to dye keratin fibres by various techniques, starting from direct dyes or pigments for non-permanent colourings or from dye precursors for permanent colourings.

Non-permanent dyeing or direct dyeing consists in dyeing the keratin fibres with dye compositions containing direct dyes. These dyes are coloured and colouring molecules that have an affinity for the keratin fibres. They are applied to the keratin fibres for a time necessary to obtain the desired colouring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, thereby making it possible to obtain colourings that are visible on dark hair.

It is also known practice to dye keratin fibres permanently by oxidation dyeing. This dyeing technique consists in applying, to the keratin fibres, a composition containing dye precursors such as oxidation bases and couplers. Under the action of an oxidizing agent, these precursors will form one or more coloured substances in the hair.

The variety of molecules used as oxidation bases and couplers allows a wide range of colours to be obtained, and the colourings resulting therefrom are permanent, strong and resistant to external agents, especially to light, inclement weather, washing, perspiration and rubbing.

In order to be visible on dark hair, these two dyeing techniques require prior or simultaneous bleaching of the keratin fibres. This bleaching step, carried out with an oxidizing agent such as hydrogen peroxide or persalts, results in considerable degradation of the keratin fibres, which adversely affects their cosmetic properties. The hair then has a tendency to become coarse, more difficult to disentangle and more brittle.

Another dyeing method consists in using pigments. Specifically, the use of pigment at the surface of keratin fibres generally makes it possible to obtain colourings that are visible on dark hair, since the surface pigment masks the natural colour of the fibre. The use of pigment for dyeing keratin fibres is, for example, described in patent application FR 2 741 530, which recommends using, for temporary dyeing of keratin fibres, a composition comprising at least one dispersion of particles of film-forming polymer comprising at least one acid function and at least one pigment dispersed in the continuous phase of said dispersion.

The colourings obtained by this dyeing method have the drawback of having poor shampoo resistance.

Furthermore, it is known to produce coloured coatings of the hair using a composition comprising an electrophilic monomer of cyanoacrylate type, and a pigment, in particular in document EP 1 649 898. Such a composition makes it possible to obtain completely coated and non-greasy hair. However, the coating obtained is not completely satisfactory in the face of external agents, such as washing and perspiration. Furthermore, the coating obtained is sensitive to fatty substances, such as sebum.

It is also possible to colour the hair (coloured coating) using a pressure-sensitive adhesive silicone copolymer, in particular a copolymer based on silicone resin and on silicone fluid. Once deposited on the hair, these copolymers have the advantage of providing colour in a long-lasting manner. On the other hand, the hair treated is rather coarse to the touch.

Thus, the objective of the present invention is to develop a composition for dyeing keratin fibres, in particular human keratin fibres such as the hair, which makes it possible to obtain a homogeneous and smooth coloured coating on the hair, and also hairs that are completely individualized, while forming a coating that is resistant to shampoo and to the various attacks to which the hair may be subjected, without degrading the keratin fibres.

This objective is achieved with the present invention, one subject of which is a composition for dyeing keratin fibres, especially human keratin fibres such as the hair, comprising at least one aqueous dispersion of particles of hybrid film-forming hydrophobic acrylic polymer, at least one linear block silicone copolymer and at least one pigment.

Another subject of the present invention is a method for dyeing keratin fibres, especially human keratin fibres such as the hair, comprising the application to said fibres of a composition as defined above.

The term "at least one" is understood to mean "one or more".

The term "comprising a" is understood to mean "comprising at least one", unless otherwise specified.

Through the use of such a composition, coloured coatings are obtained on the keratin fibres that make it possible to obtain a colouring that is visible on all types of hair in a shampoo-resistant manner while preserving the physical qualities of the keratin fibre. Such a coating is in particular resistant to the external attacks which the hair may be subjected to, such as blow drying and perspiration. It makes it possible in particular to obtain a smooth and homogeneous deposition. Furthermore, it has been observed, surprisingly, that the hair remained completely individualized and could be styled without problems, and that the styling properties contributed to the fibre were shampoo-resistant.

The term "individualized hairs" is understood to mean hairs which, after application of the composition and drying, are not stuck together (or are all separated from one another) and thus do not form clumps of hair, the coating being formed around virtually each hair.

Dyeing Composition

Aqueous Dispersion of Particles of Hybrid Acrylic Hydrophobic Film-Forming Polymer The term "polymer" Is understood to mean, within the meaning of the invention, a compound corresponding to the repetition of one or more units (these units resulting from compounds known as monomers). This or these unit(s) is (are) repeated at least twice and preferably at least 3 times.

The term "film-forming polymer" is understood to mean a polymer which is capable of forming, by itself alone or in the presence of an additional film-forming agent, a macroscopically continuous film on a support, in particular on keratin substances, and preferably a cohesive film.

The term "hydrophobic polymer" is understood to mean a polymer having a solubility in water at 25° C. of less than 1% by weight.

The dispersion can be a simple dispersion in the aqueous medium of the composition.

Mention may be made, as specific case of dispersions, of latexes.

The term "hybrid acrylic polymer" is understood to mean, within the meaning of the present invention, a polymer synthesized from at least one compound (i) chosen from monomers having at least one (meth)acrylic acid group and/or from esters of these acid monomers and/or from amides of these acid monomers and from at least one compound (ii) other than the compounds (i) i.e. which does not comprises (meth)acrylic acid group and/or esters of these acid monomers and/or amides of these acid monomers.

The (meth)acrylic acid esters (also known as (meth)acrylates) are advantageously chosen from alkyl (meth)acrylates, in particular $C_1$-$C_{30}$, preferably $C_1$-$C_{20}$ and better still $C_1$-$C_{10}$ alkyl (meth)acrylates, aryl (meth)acrylates, in particular $C_6$-$C_{10}$ aryl (meth)acrylates, or hydroxyalkyl (meth)acrylates, in particular $C_2$-$C_6$ hydroxyalkyl (meth)acrylates.

Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate.

Mention may be made, among aryl (meth)acrylates, of benzyl acrylate and phenyl acrylate.

The (meth)acrylic acid esters which are particularly preferred are the alkyl (meth)acrylates.

According to the present invention, the alkyl group of the esters can be either fluorinated or perfluorinated, that is to say that some or all of the hydrogen atoms of the alkyl group are replaced with fluorine atoms.

Mention may be made, as amides of the acid monomers, for example, of (meth)acrylamides and in particular N-alkyl (meth)acrylamides, especially N—($C_2$-$C_{12}$ alkyl)(meth)acrylamides. Mention may be made, among N-alkyl(meth)acrylamides, of N-ethylacrylamide, N-(t-butyl)acrylamide, N-(t-octyl)acrylamide and N-undecylacrylamide.

Mention will be made, as compounds (ii) other than the compounds (i), for example, of the styrene monomers.

In particular, the acrylic polymer can be a styrene/acrylate copolymer and especially a polymer chosen from the copolymers resulting from the polymerization of at least one styrene monomer and at least one $C_1$-$C_{20}$ and preferably $C_1$-$C_{10}$ alkyl acrylate monomer.

Mention may be made, as styrene monomer which can be used in the invention, of styrene or α-methylstyrene and preferably styrene.

The $C_1$-$C_{10}$ alkyl acrylate monomer can be chosen from methyl acrylate, ethyl acrylate, propyl acrylate, butyl acrylate, hexyl acrylate, octyl acrylate or 2-ethylhexyl acrylate.

Mention may be made, as acrylic polymer synthesized with styrene compound, of the styrene/acrylate(s) copolymers sold under the name Joncryl 77 by BASF, under the name Yodosol GH41F by Akzo Nobel and under the name Syntran 5760 CG by Interpolymer.

Mention may also be made, as compound (ii), of the compounds which interact by a process other than the radical polymerisation of unsaturated compounds or the compounds resulting from such a process. Such a process can, for example, be a polycondensation. Mention may be made, as polycondensation, of the formation of polyurethanes, polyesters or polyamides. In addition to the acrylic monomer or monomers, the hybrid hydrophobic film-forming polymer of the invention will then comprise the compound resulting from the condensation process or the compounds which interact in the polycondensation process.

Mention may in particular be made, as hydrophobic film-forming hybrid acrylic copolymers of this type, of the copolymer sold under the reference Hybridur 875 Polymer Dispersion by Air Products and Chemicals.

Use may also be made, as hybrid film-forming hydrophobic acrylic copolymer, of the product sold under the reference Primal HG 1000 by Dow.

The hybrid hydrophobic film-forming acrylic polymer or polymers in aqueous dispersion can be present in a content, as active material, ranging from 0.1% to 30% by weight, more particularly from 0.5% to 20% by weight and preferably from 1% to 15% by weight, relative to the total weight of the composition.

Linear Block Silicone Copolymer

The silicone copolymer used in the composition according to the invention is a linear block copolymer, that is to say an uncrosslinked copolymer, obtained by chain extension and not by crosslinking.

The term "block copolymer" (or "sequential copolymer") denotes a polymer comprising at least two distinct blocks (sequences). Each block of the polymer results from one type of monomer or from several types of different monomers. This means that each block can be composed of a homopolymer or of a copolymer, it being possible for this copolymer constituting the block to be in its turn a random or alternating copolymer.

The silicone copolymer used in the composition according to the invention preferably comprises at least two distinct silicone blocks, each block of the polymer resulting from one type of silicone monomer or from several types of different silicone monomers, such as mentioned below.

It should also be noted that the copolymer is "linear"; in other words, the structure of the polymer is neither branched nor star-branched nor grafted.

The linear block silicone copolymer is advantageously provided in the form of particles in dispersion in an aqueous medium.

The aqueous dispersion of block copolymer particles is a silicone-in-water (Si/W) emulsion, the oily globules of which are composed of a silicone of high viscosity, so that these globules appear to form as "soft particles".

The size of the linear block silicone copolymer particles can vary widely.

Preferably, in the present patent application, the linear block silicone copolymer particles generally exhibit a number-average size of less than or equal to 2 microns and preferably of less than or equal to 1 micron.

The aqueous dispersions of linear block silicone copolymer particles used in the composition according to the Invention can be chosen in particular from those described in the document EP-A-874 017, the teaching of which is incorporated here by reference. According to this document, it is possible in particular to obtain the silicone copolymers constituting these particles by a chain extension reaction in the presence of a catalyst, starting from at least:

(a) one polysiloxane (i) having at least one reactive group and preferably one or two reactive groups per molecule; and (b) one organosilicone compound (ii) which reacts with the polysiloxane (i) by a chain extension reaction.

In particular, the polysiloxane (i) is chosen from the compounds of formula (I):

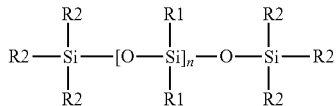

in which $R_1$ and $R_2$ represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" is understood to mean any group capable of reacting with the organosilicone compound (ii) to form a block copolymer. Mention may be made, as reactive groups, of hydrogen; aliphatically unsaturated groups, and in particular vinyl, allyl or hexenyl groups; the hydroxyl group; alkoxy groups, such as methoxy, ethoxy or propoxy groups; alkoxy-alkoxy groups; the acetoxy group; amino groups, and mixtures thereof. Preferably, more than 90% and better still more than 98% of reactive groups are at the chain end, that is to say that the $R_2$ radicals generally constitute more than 90% and even 98% of the reactive groups.

n can in particular be an integer ranging from 2 to 100, preferably from 10 to 30 and better still from 15 to 25.

The polysiloxanes of formula (I) are linear polymers, that is to say comprising few branchings and generally less than 2 mol % of siloxane units. Furthermore, the $R_1$ and $R_2$ groups can optionally be substituted by amino groups, epoxy groups or sulfur-comprising, silicon-comprising or oxygen-comprising groups.

Preferably, at least 80% of the $R_1$ groups are alkyl groups and better still methyl groups.

Preferably, the reactive group $R_2$ at the chain end is an aliphatically unsaturated group and in particular a vinyl group.

Mention may in particular be made, as polysiloxanes (i), of dimethylvinylsiloxy-polydimethylsiloxane, a compound of formula (I) in which the $R_1$ radicals are methyl radicals and the $R_2$ radicals at the chain end are vinyl radicals while the other two $R_2$ radicals are methyl radicals.

The organosilicone compound (ii) can be chosen from polysiloxanes of formula (I) or compounds acting as chain-extending agent. If it is a compound of formula (I), the polysiloxane (i) will comprise a first reactive group and the organosilicone compound (ii) will comprise a second reactive group which will react with the first. If it is a chain-extending agent, it can be a silane, a siloxane (disiloxane or trisiloxane) or a silazane. Preferably, the organosilicone compound (ii) is a liquid organohydropolysiloxane of formula II:

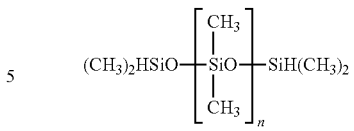

where n is an integer greater than 1 and preferably greater than 10, for example ranging from 2 to 100, preferably from 10 to 30 and better still from 15 to 25. According to a specific embodiment of the invention, n is equal to 20.

The silicone block copolymers used according to the invention are advantageously devoid of oxyalkylene group(s), in particular devoid of oxyethylene and/or oxypropylene group(s).

The catalyst of the reaction between the polysiloxane and the organosilicone compound can be chosen from metals and in particular from platinum, rhodium, tin, titanium, copper and lead. It is preferably platinum or rhodium.

The dispersion of silicone copolymer particles used in the composition according to the invention can in particular be obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture, in order for the chain-extending reaction to begin only in the dispersion.

Mention may be made, as emulsifiers capable of being used in the preparation process described above in order to obtain the aqueous dispersion of particles, of non-ionic or ionic (anionic, cationic or amphoteric) emulsifiers. They are preferably non-ionic emulsifiers which can be chosen from polyalkylene glycol ethers of fatty alcohol comprising from 8 to 30 carbon atoms and preferably from 10 to 22 carbon atoms; polyoxyalkylenated and in particular polyoxyethylenated sorbitan alkyl esters, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and mixtures thereof. The amount of emulsifier(s) is generally from 1% to 30% by weight, relative to the total weight of the reaction mixture.

The emulsifier used to obtain the aqueous dispersion of particles is preferably chosen from polyethylene glycol ethers of fatty alcohols and mixtures thereof and in particular polyethylene glycol ethers of alcohols comprising 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3, $C_{12}$-$C_{13}$ Pareth-23 and mixtures thereof.

According to a specific embodiment of the invention, the dispersion of silicone copolymer particles is obtained from dimethylvinylsiloxy-polydimethylsiloxane (or divinyldimethicone), as compound (i), and from the compound of formula (II) with preferably n=20, as compound (ii), preferably in the presence of a catalyst of platinum type, and the dispersion of particles is preferably obtained in the presence of $C_{12}$-$C_{13}$ Pareth-3 and $C_{12}$-$C_{13}$ Pareth-23, as emulsifiers.

Use may in particular be made, as dispersion of silicone copolymer particles, of the product sold under the name HMW 2220 by Dow Corning (CTFA name: divinyldimethicone/dimethicone copolymer/$C_{12}$-$C_{13}$ Pareth-3/$C_{12}$-$C_{13}$ Pareth-23), which is a 60% aqueous dispersion of divinyldimethicone/dimethicone copolymer comprising $C_{12}$-$C_{13}$ Pareth-3 and $C_{12}$-$C_{13}$ Pareth-23, said dispersion comprising approximately 60% by weight of copolymer, 2.8% by weight of $C_{12}$-$C_{13}$ Pareth-23, 2% by weight of $C_{12}$-$C_{13}$ Pareth-3 and 0.31% by weight of preservatives, the remainder to 100% being water.

The linear block silicone copolymer or copolymers can be present in an amount, as polymeric active materials, ranging from 0.1% to 30% by weight, better still from 0.5% to 20% by weight and even better still from 1% to 15% by weight, relative to the total weight of the composition.

According to one embodiment, the hybrid hydrophobic film-forming acrylic polymer or polymers and the linear block silicone copolymer or copolymers are present in a weight ratio (as polymeric active materials) of hydrophobic film-forming acrylic polymer(s) to linear block silicone copolymer(s) ranging from 0.2 to 10, better still from 0.5 to 5 and even better still from 1 to 3.

When the hybrid hydrophobic film-forming acrylic polymer has a glass transition temperature which is too high for the desired use, a plasticizer can be combined therewith so as to lower this temperature of the mixture used. The plasticizer can be chosen from the plasticizers normally used in the field of application and in particular from compounds which can be solvents for the polymer.

Preferably, the plasticizer has a molecular weight of less than or equal to 5000 g/mol, preferably of less than or equal to 2000 g/mol, preferably of less than or equal to 1000 g/mol and more preferably of less than or equal to 900 g/mol. The plasticizer advantageously has a molecular weight of greater than or equal to 100 g/mol.

Thus, the composition can additionally comprise at least one plasticizing agent. In particular, mention may be made, alone or as a mixture, of the usual plasticizers, such as:
  glycols and their derivatives, such as diethylene glycol ethyl ether, diethylene glycol methyl ether, diethylene glycol butyl ether or else diethylene glycol hexyl ether, ethylene glycol ethyl ether, ethylene glycol butyl ether or ethylene glycol hexyl ether;
  polyethylene glycols, polypropylene glycols, polyethylene glycol/polypropylene glycol copolymers and mixtures thereof, in particular polypropylene glycols of high molecular weight, for example having a molecular weight ranging from 500 to 15 000, such as, for example:
  glycol esters;
  propylene glycol derivatives and in particular propylene glycol phenyl ether, propylene glycol diacetate, dipropylene glycol ethyl ether, tripropylene glycol methyl ether, diethylene glycol methyl ether or dipropylene glycol butyl ether. Such compounds are sold by Dow Chemical under the names Dowanol PPH and Dowanol DPnB;
  acid esters, in particular carboxylic acid esters, such as citrates, phthalates, adipates, carbonates, tartrates, phosphates or sebacates;
  esters resulting from the reaction of a monocarboxylic acid of formula $R_{11}COOH$ with a diol of formula $HOR_{12}OH$ with $R_{11}$ and $R_{12}$, which are identical or different, representing a saturated or unsaturated and linear, branched or cyclic hydrocarbon chain preferably comprising from 3 to 15 carbon atoms and optionally comprising one or more heteroatoms, such as N, O or S, in particular the monoester resulting from the reaction of isobutyric acid and octanediol, such as 2,2,4-trimethyl-1,3-pentanediol, such as that sold under the reference Texanol Ester Alcohol by Eastman Chemical;
  oxyethylenated derivatives, such as oxyethylenated oils, in particular vegetable oils, such as castor oil; and mixtures thereof.

More particularly, the plasticizer can be chosen from esters of at least one carboxylic acid comprising from 1 to 7 carbon atoms and of a polyol comprising at least 4 hydroxyl groups.

The polyol can be a cyclized or non-cyclized monosaccharide-polyhydroxyaldehyde (aldose) or polyhydroxyketone (ketose). The polyol is preferably a cyclized monosaccharide in the hemiacetal form.

The polyol can be a mono- or polysaccharide comprising from 1 to 10 monosaccharide units, preferably from 1 to 4 monosaccharide units and more preferably one or two monosaccharide units. The polyol can be chosen from erythritol, xylitol, sorbitol, glucose, sucrose, lactose or maltose.

The polyol is preferably a disaccharide. Mention may be made, among disaccharides, of sucrose (also known as α-D-glucopyranosyl-(1-2)-β-D-fructofuranose), lactose (also known as β-D-galactopyranosyl-(1-4)-β-D-glucopyranose) and maltose (also known as α-D-glucopyranosyl-(1-4)-β-D-glucopyranose), and preferably of sucrose.

The ester can be composed of a polyol esterified by at least two different monocarboxylic acids or by at least three different monocarboxylic acids.

The ester can be a copolymer of two esters, in particular a copolymer i) of a sucrose substituted by benzoyl groups and ii) of a sucrose substituted by acetyl and/or isobutyryl groups.

The carboxylic acid is preferably a monocarboxylic acid comprising from 1 to 7 carbon atoms and preferably from 1 to 5 carbon atoms, for example chosen from acetic acid, n-propanoic acid, isopropanoic acid, n-butanoic acid, isobutanoic acid, tert-butanoic acid, n-pentanoic acid and benzoic acid.

The ester can be obtained from at least two different monocarboxylic acids. According to one embodiment, the acid is a linear or branched acid which is unsubstituted.

The acid is preferably chosen from acetic acid, isobutyric acid, benzoic acid and mixtures thereof.

According to a preferred embodiment, the ester is sucrose diacetate hexa(2-methylpropanoate), such as that sold under the name Sustane SAIB Food Grade Kosher by Eastman Chemical.

According to another embodiment, the plasticizer can be chosen from esters of an aliphatic or aromatic polycarboxylic acid and of an aliphatic or aromatic alcohol comprising from 1 to 10 carbon atoms.

The aliphatic or aromatic alcohol comprises from 1 to 10 carbon atoms, preferably from 1 to 8 carbon atoms, for example from 1 to 6 carbon atoms. It can be chosen from R1OH alcohols, such that R1 represents methyl, ethyl, propyl, isopropyl, butyl, hexyl, ethylhexyl, decyl, isodecyl, benzyl or benzyl substituted by an alkyl comprising from 1 to 3 carbon atoms, and mixtures thereof.

The aliphatic or aromatic polycarboxylic acid preferably comprises from 3 to 12 carbon atoms, preferably from 3 to 10 carbon atoms, preferably from 3 to 8 carbon atoms, for example 6 or 8 carbon atoms.

The aliphatic or aromatic polycarboxylic acid is advantageously chosen from dicarboxylic acids and tricarboxylic acids.

Mention may be made, among aliphatic dicarboxylic acids, of those of formula $HOOC-(CH_2)_n-COOH$, in which n is an integer ranging from 1 to 10, preferably ranging from 2 to 8, for example equal to 2, 4, 6 or 8.

Preference is given to dicarboxylic acids chosen from succinic acid, adipic acid and sebacic acid.

Mention may be made, among aromatic dicarboxylic acids, of phthalic acid.

Mention may be made, among tricarboxylic acids, of triacids which correspond to the formula:

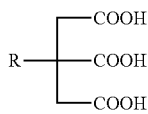

in which R represents an —H, —OH or —OCOR' group in which R' represents an alkyl group having from 1 to 6 carbon atoms. Preferably, R represents an —OCOCH$_3$ group.

The tricarboxylic acid is chosen in particular from acetylcitric acid, butyroylcitric acid or citric acid.

Use may be made, among tricarboxylic acid esters, of esters derived from citric acid (or citrates), such as tributyl acetylcitrate, triethyl acetylcitrate, triethylhexyl acetylcitrate, trihexyl acetylcitrate, trihexyl butyroylcitrate, triisodecyl citrate, triisopropyl citrate, tributyl citrate and tri(2-ethylhexyl) citrate. Mention may be made, as commercial references for plasticizers mentioned above, of the Citroflex range sold by Vertellus, with in particular Citroflex A4 and Citroflex C2.

Mention may be made, among adipic acid esters, of dibutyl adipate and di(2-ethylhexyl) adipate.

Mention may be made, among sebacic acid esters, of dibutyl sebacate, di(2-ethylhexyl) sebacate, diethyl sebacate and diisopropyl sebacate.

Mention may be made, among succinic acid esters, of di(2-ethylhexyl) succinate and diethyl succinate.

Mention may be made, among phthalic acid esters, of benzyl butyl phthalate, dibutyl phthalate, diethylhexyl phthalate, diethyl phthalate and dimethyl phthalate.

Advantageously, the plasticizer or plasticizers can be present in the composition in a content such that the weight ratio of the hybrid hydrophobic film-forming acrylic polymer or polymers to the plasticizer or plasticizers varies from 0.5 to 100, preferably from 1 to 50 and preferably from 1 to 10.

Pigments

The composition comprises pigments.

Such a composition makes it possible to obtain long-lasting coloured coatings, without damaging the keratin fibres.

The term "pigment" is understood to mean white or coloured particles of any shape which are insoluble in the composition in which they are present.

The pigments which can be used are chosen in particular from organic and/or inorganic pigments known in the art, in particular those which are described in Kirk-Othmer's Encyclopedia of Chemical Technology and in Ullmann's Encyclopedia of Industrial Chemistry.

They can be natural, of natural origin, or not.

These pigments can be provided in the pigment powder or paste form. They can be coated or uncoated.

The pigments can be chosen, for example, from inorganic pigments, organic pigments, lakes, special-effect pigments, such as pearlescent agents or glitter, and mixtures thereof.

The pigment can be an inorganic pigment. The term "Inorganic pigment" is understood to mean any pigment which corresponds to the definition of Ullmann's Encyclopedia in the "Inorganic Pigment" chapter. Mention may be made, among inorganic pigments of use in the present invention, of ochres, such as red ochre (clay (in particular kaolinite) and iron hydroxide (for example haematite)), brown ochre (clay (in particular kaolinite) and limonite) or yellow ochre (clay (in particular kaolinite) and goethite); titanium dioxide, optionally surface-treated; zirconium or cerium oxides; zinc, (black, yellow or red) iron or chromium oxides; manganese violet, ultramarine blue, chromium hydrate and ferric blue; or metal powders, such as aluminium powder or copper powder.

Mention may also be made of alkaline earth metal carbonates (such as calcium carbonate or magnesium carbonate), silicon dioxide, quartz and any other compound used as inert filler in cosmetic compositions, provided that these compounds contribute colour or whiteness to the composition under the conditions under which they are employed.

The pigment can be an organic pigment. The term "organic pigment" is understood to mean any pigment which corresponds to the definition of Ullmann's Encyclopedia in the "Organic Pigment" chapter.

The organic pigment can in particular be chosen from nitroso, nitro, azo, xanthene, pyrene, quinoline, anthraquinone, fluoran or phthalocyanine compounds, compounds of metal complex type, or isoindolinone, isoindoline, quinacridone, perinone, perylene, diketopyrrolopyrrole, indigo, thioindigo, dioxazine, triphenylmethane or quinophthalone compounds.

Use may also be made of any inorganic or organic compound that is insoluble in the composition and that is conventional in the cosmetics field, provided that these compounds contribute colour or whiteness to the composition under the conditions under which they are employed, for example guanine, which, according to the refractive index of the composition, is a pigment.

In particular, the white or coloured organic pigments can be chosen from carmine, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, or the pigments obtained by oxidative polymerization of indole or phenol derivatives, as are described in Patent FR 2 679 771.

Mention may also be made, as example, of pigment pastes formed of organic pigment, such as the products sold by Hoechst under the names:

Cosmenyl Yellow 10G: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Cosmenyl Carmine FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260);
Cosmenyl Black R: Pigment Black 7 (CI 77266).

The pigments in accordance with the invention can also be in the form of composite pigments, as are described in Patent EP 1 184 426. These composite pigments can be composed in particular of particles comprising an inorganic core, at least one binder, which provides for the attachment of the organic pigments to the core, and at least one organic pigment which at least partially covers the core.

The organic pigment can also be a lake. The term "lake" is understood to mean dyes adsorbed onto insoluble particles, the combination thus obtained remaining insoluble during use.

The inorganic substrates onto which the dyes are adsorbed are, for example, alumina, silica, calcium sodium borosilicate, calcium aluminium borosilicate and aluminium.

Mention may be made, among the dyes, of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 47 005), D&C Green 3 (CI 42 053) or D&C Blue 1 (CI 42 090).

An example of a lake that may be mentioned is the product known under the following name: D&C Red 7 (CI 15 850:1).

The pigment can also be a special-effect pigment. The term "special-effect pigments" is understood to mean pigments which generally create a coloured appearance (characterized by a certain shade, a certain vividness and a certain brightness) which is not uniform and which changes as a function of the conditions of observation (light, temperature, angles of observation, etc.). They thus contrast with coloured pigments that afford a conventional uniform opaque, semi-transparent or transparent shade.

There exist several types of special-effect pigments: those with a low refractive index, such as fluorescent, photochromic or thermochromic pigments, and those with a higher refractive index, such as pearlescent agents, interferential pigments or glitter.

Mention may be made, as examples of special-effect pigments, of pearlescent pigments, such as mica covered with titanium dioxide or with bismuth oxychloride, coloured pearlescent pigments, such as mica covered with titanium dioxide and with iron oxides, mica covered with iron oxide, mica covered with titanium dioxide and in particular with ferric blue or chromium oxide or mica covered with titanium dioxide and with an organic pigment as defined above, and pearlescent pigments based on bismuth oxychloride. Mention may be made, as pearlescent pigments, of the following pearlescent agents: Cellini sold by Engelhard (mica-$TiO_2$-lake), Prestige sold by Eckart (mica-$TiO_2$), Prestige Bronze sold by Eckart (mica-$Fe_2O_3$) or Colorona sold by Merck (mica-$TiOrFe_2O_3$).

Mention may also be made of pearlescent agents of gold colour sold in particular by Engelhard under the names of Brilliant Gold 212G (Timica), Gold 222C (Cloisonne), Sparkle Gold (Timica), Gold 4504 (Chromalite) and Monarch Gold 233X (Cloisonne); bronze pearlescent agents sold in particular by Merck under the names Bronze Fine (17384) (Colorona) and Bronze (17353) (Colorona) and by Engelhard under the name Super Bronze (Cloisonne); orange pearlescent agents sold in particular by Engelhard under the names Orange 363C (Cloisonne) and Orange MCR 101 (Cosmica) and by Merck under the names Passion Orange (Colorona) and Matte Orange (17449) (Microna); brown-coloured pearlescent agents sold in particular by Engelhard under the names Nu-Antique Copper 340XB (Cloisonne) and Brown CL4509 (Chromalite); pearlescent agents with a copper glint sold in particular by Engelhard under the name Copper 340A (Timica); pearlescent agents with a red glint sold in particular by Merck under the name Sienna Fine (17386) (Colorona); pearlescent agents with a yellow glint sold in particular by Engelhard under the name Yellow (4502) (Chromalite); red-coloured pearlescent agents with a gold glint sold in particular by Engelhard under the name Sunstone G012 (Gemtone); pink pearlescent agents sold in particular by Engelhard under the name Tan Opale G005 (Gemtone); black pearlescent agents with a gold glint sold in particular by Engelhard under the name Nu-Antique Bronze 240 AB (Timica); blue pearlescent agents sold in particular by Merck under the name Matte Blue (17433) (Microna); white pearlescent agents with a silvery glint sold in particular by Merck under the name Xirona Silver; golden green pinkish orangey pearlescent agents sold in particular by Merck under the name Indian Summer (Xirona); and mixtures thereof.

Mention may also be made, still as examples of pearlescent agents, of particles comprising a borosilicate substrate coated with titanium oxide.

Particles having a glass substrate coated with titanium oxide are especially sold under the name Metashine MC1080RY by the company Toyal.

Finally, mention may also be made, as examples of pearlescent agents, of polyethylene terephthalate glitter, in particular that sold by Meadowbrook Inventions under the name Silver 1P 0.004×0.004 (silver glitter).

It is also possible to envisage multilayer pigments based on synthetic substrates, such as alumina, silica, calcium sodium borosilicate, calcium aluminium borosilicate and aluminium.

The special-effect pigments can also be chosen from reflective particles, that is to say in particular particles having a size, a structure, in particular a thickness of the layer or layers of which it is composed and their physical and chemical nature, and a surface condition which allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles can be selected so as not to detrimentally affect, to a significant extent, the colouring effect generated by the colouring agents which are combined with them and more particularly so as to optimize this effect in terms of colour rendition. They can more particularly have a yellow, pink, red, bronze, orangey, brown, gold and/or coppery colour or glint.

These particles may have varied forms and may especially be in platelet or globular form, in particular in spherical form.

The reflective particles, whatever their form, may or may not have a multilayer structure and, in the case of a multilayer structure, may have, for example, at least one layer of uniform thickness, in particular of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or inorganic materials.

More particularity, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described in particular in the documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name MICROGLASS METASHINE REFSX 2025 PS by the company TOYAL. Particles with a glass substrate coated with nickel/chromium/molybdenum alloy are sold under the name CRYSTAL STAR GF 550 and GF 2525 by this same company.

Use may also be made of particles comprising a metallic substrate such as silver, aluminium, iron, chromium, nickel, molybdenum, gold, copper, zinc, tin, manganese, steel, bronze or titanium, said substrate being coated with at least one layer of at least one metal oxide such as titanium oxide, aluminium oxide, iron oxide, cerium oxide, chromium oxide or silicon oxides, and mixtures thereof.

Mention may be made, as examples, of aluminium powder, bronze powder or copper powder coated with $SiO_2$ sold under the name Visionaire by Eckart.

Mention may also be made of pigments with an interference effect which are not attached to a substrate, such as liquid crystals (Helicones HC from Wacker), interference holographic glitter (Geometric Pigments or Spectra f/x from Spectratek).

Special-effect pigments also include fluorescent pigments, whether these are substances which are fluorescent in daylight or which produce ultraviolet fluorescence, phosphorescent pigments, photochromic pigments, thermochromic pigments and quantum dots, for example sold by Quantum Dots Corporation.

Quantum dots are luminescent semiconductor nanoparticles capable of emitting, under light excitation, radiation exhibiting a wavelength of between 400 nm and 700 nm. These nanoparticles are known from the literature. In particular, they may be manufactured according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterisation of a size series of highly luminescent nanocristallites", Journal of Physical Chemistry B, vol. 101, 1997, pp 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pp 7019-7029.

The variety of the pigments which can be used in the present invention makes it possible to obtain a rich palette of colours and also specific optical effects, such as metallic effects or interference effects.

The size of the pigment used in the cosmetic composition according to the present invention is generally between 10 nm and 200 μm, preferably between 20 nm and 80 μm and more preferably between 30 nm and 50 μm.

The pigments may be dispersed in the product by means of a dispersant.

The dispersant serves to protect the dispersed particles from the agglomeration or flocculation thereof. This dispersant can be a surfactant, an oligomer, a polymer or a mixture of several thereof, bearing one or more functionalities having a strong affinity for the surface of the particles to be dispersed. In particular, they can become attached physically or chemically to the surface of the pigments. These dispersants additionally have at least one functional group compatible with or soluble in the continuous medium. Use is made in particular of esters of 12-hydroxystearic acid, in particular, and of $C_8$ to $C_{20}$ fatty acid and of polyol, for instance glycerol or diglycerol, such as poly(12-hydroxystearic acid) stearate with a molecular weight of approximately 750 g/mol, such as that sold under the name of Solsperse 21 000 by Avecia, polyglyceryl-2 dipolyhydroxystearate (CTFA name), sold under the reference Dehymyls PGPH by Henkel, or polyhydroxystearic acid, such as that sold under the reference Aracel P100 by Unigema, and mixtures thereof.

Mention may be made, as another dispersant which can be used in the compositions of the invention, of the quaternary ammonium derivatives of polycondensed fatty acids, such as Solsperse 17 000, sold by Avecia, or polydimethylsiloxane/ oxypropylene mixtures, such as those sold by Dow Corning under the references DC2-5185 and DC2-5225 C.

The pigments used in the cosmetic composition according to the invention may be surface-treated with an organic agent.

Thus, the pigments surface-treated beforehand of use in the context of the invention are pigments which have been completely or partially subjected to a surface treatment of chemical, electronic, electrochemical, mechanochemical or mechanical nature with an organic agent, such as those which are described in particular in Cosmetics and Toiletries, February 1990, vol. 105, pp. 53-64, before being dispersed in the composition in accordance with the invention. These organic agents can, for example, be chosen from waxes, for example camauba wax and beeswax; fatty acids, fatty alcohols and their derivatives, such as stearic acid, hydroxystearic acid, stearyl alcohol, hydroxystearyl alcohol, lauric acid and their derivatives; anionic surfactants; lecithins; sodium, potassium, magnesium, iron, titanium, zinc or aluminium salts of fatty acids, for example aluminium stearate or laurate; metal alkoxides; polyethylene; (meth) acrylic polymers, for example polymethyl methacrylates; polymers and copolymers comprising acrylate units; alkanolamines; silicone compounds, for example silicones or polydimethylsiloxanes; fluorinated organic compounds, for example perfluoroalkyl ethers; or fluorosilicone compounds.

The surface-treated pigments of use in the cosmetic composition according to the invention may also have been treated with a mixture of these compounds and/or have undergone several surface treatments.

The surface-treated pigments of use in the context of the present invention can be prepared according to surface treatment techniques well known to a person skilled in the art or found as such commercially.

Preferably, the surface-treated pigments are covered with an organic layer.

The organic agent with which the pigments are treated can be deposited on the pigments by solvent evaporation, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is described in particular in U.S. Pat. No. 4,578,266.

Preferably, use will be made of an organic agent covalently bonded to the pigments.

The agent for the surface treatment can represent from 0.1% to 50% by weight, preferably from 0.5% to 30% by weight and more preferentially still from 1% to 10% by weight, of the total weight of the surface-treated pigment.

Preferably, the surface treatments of the pigments are chosen from the following treatments:
- a PEG-silicone treatment, for instance the AQ surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a magnesium myristate treatment, for instance the MM surface treatment sold by LCW;
- an aluminium dimyristate treatment, for instance the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrosiloxane/perfluoroalkyl phosphate treatment, such as the FS01 surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- an acrylate copolymer treatment, for instance the APD surface treatment sold by Daito.
- a perfluoroalkyl phosphate/isopropyl titanium triisostearate treatment, such as the PF+ITT surface treatment sold by Daito.

Preferably, the pigment is chosen from inorganic pigments or inorganic/organic mixed pigments.

The amount of pigment(s) can vary from 0.01% to 30% by weight, more particularly from 0.05% to 20% by weight and preferably from 0.1% to 15% by weight, relative to the total weight of the composition.

The composition of the invention can comprise other coloured or colouring entities, such as direct dyes or dye precursors.

Thickener

According to a preferred embodiment, the composition according to the invention comprises at least one thickener chosen from polymeric or non-polymeric, inorganic or organic thickeners and mixtures thereof.

The term "thickener" is understood to mean a compound which modifies the rheology of the medium into which it is incorporated.

According to a specific embodiment of the invention, the composition comprises at least one inorganic thickener.

Preferably, the thickener or thickeners is/are chosen from fumed silica, clays or mixtures thereof.

The fumed silicas can be obtained by high-temperature pyrolysis of a volatile silicon compound in an oxyhydrogen flame, producing a finely divided silica. This process makes it possible in particular to obtain hydrophilic silicas which have a large number of silanol groups at their surface. Such hydrophilic silicas are sold for example under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the said silica via a chemical reaction which brings about a reduction in the number of silanol groups. It is possible in particular to replace silanol groups with hydrophobic groups: a hydrophobic silica is then obtained.

The hydrophobic groups can be:
- trimethylsiloxyl groups, which are obtained in particular by treating fumed silica in the presence of hexamethyldisilazane. Silicas thus treated are known as "Silica silylate" according to the CTFA ($6^{th}$ edition, 1995). They are sold for example under the references Aerosil R812® by Degussa and Cab-O-Sil TS-530® by Cabot.
- dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA ($6^{th}$ edition, 1995). They are sold for example under the references Aerosil R972® and Aerosil R974® by Degussa, and Cab-O-Sil TS-610® and Cab-O-Sil TS-720® by Cabot.

The fumed silica preferably has a particle size that may be nanometric to micrometric, for example ranging from about 5 to 200 nm.

Clays are well known products which are described, for example, in the publication "Minéralogie des argiles" [Mineralogy of Clays], S. Caillbre, S. Hénin and M. Rautureau, 2nd Edition, 1982, Masson.

Clays are silicates containing a cation which can be chosen from calcium, magnesium, aluminium, sodium, potassium or lithium cations, and mixtures thereof.

Mention may be made, as examples of such products, of clays of the family of the smectites, such as montmorillonites, hectorites, bentonites, beidellites or saponites, and also of the family of the vermiculites, stevensite or chlorites.

These clays can be of natural or synthetic origin. Use is preferably made of clays which are cosmetically compatible and acceptable with keratin substances.

Mention may be made, as clay which can be used according to the invention, of synthetic hectorites (also known as laponites), such as the products sold by Laporte under the name Laponite XLG, Laponite RD and Laponite RDS (these products are sodium magnesium silicates and in particular lithium magnesium sodium silicates); bentonites, such as the product sold under the name Bentone HC by Rheox; magnesium aluminium silicates, in particular hydrated, such as the product sold by R.T. Vanderbilt Company under the name Veegum Ultra, or calcium silicates and in particular that in synthetic form sold by the company CELITE ET WALSH ASS under the name Micro-Cel C.

The organophilic clay can be chosen from montmorillonite, bentonite, hectorite, attapulgite or sepiolite, and mixtures thereof. The clay is preferably a bentonite or a hectorite.

These clays can be modified with a chemical compound chosen from quaternary amines, tertiary amines, amine acetates, imidazolines, amine soaps, fatty sulfates, alkylarylsulfonates, amine oxides and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The thickener can also be chosen from organic compounds.

Mention may be made, for example, of the following polymeric or non-polymeric products:

$C_{10}$-$C_{30}$ fatty amides, such as lauric acid diethanolamide, the polyglyceryl (meth)acrylate polymers sold under the names Hispagel or Lubragel by the companies Hispano Qimica or Guardian, polyvinylpyrrolidone, polyvinyl alcohol, crosslinked acrylamide polymers and copolymers, such as those sold under the names PAS 5161 or Bozepol C by Hoechst or Sepigel 305 by SEPPIC, the crosslinked methacryloyloxyethyltrimethylammonium chloride homopolymers sold under the name Salcare SC95 by Allied Colloid, associative polymers and in particular associative polyurethanes.

Such thickeners are described in particular in Application EP-A-1 400 234.

Preferably, the composition comprises at least one inorganic thickener which is preferably chosen from days and more advantageously still from smectites.

The thickener is present in the composition in a total content ranging from 0.1% to 10% by weight, relative to the weight of the composition.

The composition according to the invention comprises water, which can preferably be present in a content ranging from 20% to 98% by weight, relative to the weight of the composition.

The compositions can also comprise at least one agent commonly used in cosmetics, for example chosen from reducing agents, fatty substances, organic solvents or oils, softening agents, anti-foaming agents, moisturizing agents, UV screening agents, peptizing agents, solubilizing agents, fragrances, anionic, cationic, non-ionic or amphoteric surfactants, proteins, vitamins, propellants, oxyethylenated or non-oxyethylenated waxes, paraffins or $C_{10}$-$C_{30}$ fatty acids, such as stearic acid or lauric acid.

The above additives are generally present in an amount for each of them of between 0.01% and 20% by weight, relative to the weight of the composition.

Of course, a person skilled in the art will take care to choose this or these optional additive(s) so that the advantageous properties intrinsically attached to the formation of the coating in accordance with the invention are not, or not substantially, detrimentally affected.

The composition according to the invention can be provided in particular in the form of a suspension, a dispersion, a gel, an emulsion, in particular an oil-in-water (O/W), water-in-oil (W/O) or multiple (W/O/W or polyol/O/W or O/W/O) emulsion, a cream, a foam, a stick, a dispersion of vesicles, in particular of ionic or non-ionic lipids, a two-phase or multiphase lotion, a spray or a paste. The composition can also be provided in the form of a lacquer.

A person skilled in the art can choose the appropriate formulation form, and also its method of preparation, on the basis of his general knowledge, taking into account first the nature of the constituents used, in particular their solubility in the support, and secondly the application envisaged for the composition.

Process

The composition described above can be employed on dry or wet keratin fibres and also on any type of fibre, light or dark, natural or dyed, or permanent-waved, bleached or straightened.

According to a specific embodiment of the method of the invention, the fibres are washed before application of the composition described above.

The application to the fibres can be carried out by any conventional means, in particular using a comb, a brush, including a fine brush, or the fingers.

After the application of the composition, the fibres can be left to dry or dried, for example at a temperature of greater than or equal to 30° C. According to a specific embodiment, this temperature is greater than 40° C. According to a specific embodiment, this temperature is greater than 45° C. and less than 220° C.

The drying, if it is employed, can be carried out immediately after the application or after a leave-in time which can range from 1 minute to 30 minutes.

Preferably, if the fibres are dried, they are dried with, in addition to a supply of heat, a stream of air. This stream of air during the drying makes it possible to improve the individualization of the coating.

During the drying, a mechanical action can be exerted on the locks, such as combing, brushing or running the fingers through the hair. This operation can likewise be carried out once the fibres have dried, naturally or otherwise.

The drying stage of the method of the invention can be carried out with a hood dryer, a hair dryer, hair straighteners, a Climazone, etc.

When the drying stage is carried out with a hood dryer or a hair dryer, the drying temperature is between 40° C. and 110° C. and preferably between 50° C. and 90° C.

When the drying stage is carried out with hair straighteners, the drying temperature is between 110° C. and 220° C. and preferably between 140° C. and 200° C.

Once the drying is complete, a final rinsing or shampooing can optionally be carried out.

The invention will be illustrated more fully with the aid of the non-limiting examples that follow. Unless otherwise mentioned, the amounts indicated are expressed in grams.

EXAMPLES

Composition Examples

| Composition A | |
|---|---|
| Styrene/acrylates copolymer in aqueous dispersion, sold by BASF under the name Joncryl 77 | 21.2 g, i.e. 10% as AM |
| Divinyldimethicone/dimethicone copolymer in aqueous emulsion, sold by Dow Corning under the reference HMW 2220 Non-Ionic Emulsion | 8.3 g, i.e. 5% as AM |
| Black 2 in aqueous dispersion, from Daito Kasei Kogyo under the name WD-CB2 | 10 g, i.e. 2.5% AM |
| Water | q.s. 100 g |

0.6 g of composition A is applied to 1 g of a lock of white hair.

After a few seconds, the lock of hair is dry, the hair is coloured and the colour is homogenous and resistant to several shampooing operations.

The hair can be individualized with the fingers or using a comb and/or a brush.

A dyed lock is obtained, the hairs of which are individualized and the colour of which is shampoo-resistant.

| Composition B | |
|---|---|
| Styrene/acrylates copolymer in aqueous dispersion, sold by BASF under the name Joncryl 77 | 21.2 g, i.e. 10% as AM |
| Divinyldimethicone/dimethicone copolymer in aqueous emulsion, sold by Dow Corning under the reference HMW 2220 Non-Ionic Emulsion | 8.3 g, i.e. 5% as AM |
| Clay (Magnesium Aluminium Silicate), sold by Vanderbilt under the name Veegum granules | 2 g |
| Pearlescent agent formed of mica coated with brown iron oxide, sold by Eckart under the name Prestige Soft Bronze | 6 g |
| Water | q.s. 100 g |

0.7 g of composition B is applied to a 1 g lock of hair having a tonal level of 4.

After a few seconds, the lock of hair is dry, the hair is coloured and the colour is homogenous and resistant to several shampooing operations.

The hair can be individualized with the fingers or using a comb and/or a brush.

| Composition C | |
|---|---|
| Styrene/acrylates copolymer in aqueous dispersion, sold by BASF under the name Joncryl 77 | 20 g, i.e. 9.43% as AM |
| Divinyldimethicone/dimethicone copolymer in aqueous emulsion, sold by Dow Corning under the reference HMW 2220 Non-Ionic Emulsion | 7.9 g, i.e. 4.76% as AM |
| Clay (Magnesium Aluminium Silicate), sold by Vanderbilt under the name Veegum granules | 1.8 g |
| Black 2 in aqueous dispersion, from Daito Kasei Kogyo under the name WD-CB2 | 9 g, i.e. 2.25% as AM |
| Water | q.s. 100 g |

0.6 g of composition C is applied to a 1 g lock of white hair.

After a few seconds, the lock of hair is dry, the hair is coloured and the colour is homogenous and resistant to several shampooing operations.

The hair can be individualized with the fingers or using a comb and/or a brush.

Comparative Example

The following composition were prepared: composition D according to the invention contains a hybrid film-forming hydrophobic acrylic polymer, composition E contains a PDMS grafted alkyl methacrylate copolymer which is not hybrid.

| | D (invention) | E |
|---|---|---|
| Divinyldimethicone/dimethicone copolymer in aqueous emulsion, sold by Dow Corning under the reference HMW 2220 Non-Ionic Emulsion | 6% as AM | 6% as AM |
| Styrene/acrylates copolymer in aqueous dispersion, sold by BASF under the name Joncryl 77 | 11.75 as AM | — |
| Poly dimethylsiloxane grafted alkyl methacrylate copolymer (KP-561 P - Shin Etsu) | — | 11.75 as AM |
| Pearlescent agent formed of mica coated with brown iron oxide (Prestige Soft Bronze - Eckart) | 7 | 7 |
| Isododecane | 25 | 25 |
| Water | Qs 100 | Qs 100 |

Each composition is deposited on a lock of permanent-waved grey hair containing 90% white hairs, with 0.5 g of composition for 1 g of hair, the composition being applied uniformly all along the lock. After a few seconds, the lock of hair is dried with a hair drier and a brush, then the hair is combed.

Individualization: after being combed, the hair treated with composition D is perfectly individualized, while the hair treated with composition E is sticked together and forms clumps.

Persistence of the Coating

An important deposit is observed on the brush which was used for drying the hair lock treated with composition E. There is no deposit for the hair treated with composition D. Furthermore, an important deposit is observed on the fingers after running them through the hair lock treated with composition E, while no deposit was noticed on the fingers with the hair treated with composition D.

After the above mentioned evaluations, the locks of hair treated with compositions D and E are washed one time with a standard shampoo.

Colorimetric measurements are made before and after shampoo, using a spectrocolorimeter Konica Minolta CM 3600d (D65, 10°, specular components included) in the L*a*b* system.

According to this system, L* indicates the lightness of the color of the hair. The chromaticity coordinates are expressed by the parameters a* and b*, a* indicating the axis of red/green shades and b* the axis of yellow/blue shades.

The persistence of the coating toward shampoo is represented by the difference of color ΔE between colored hair before shampoo and colored hair after shampoo. The lower the ΔE value, the better the persistence of the coating is. ΔE corresponds to $[(L^*_{BP}-L^*_{BN})^2+(a^*_{BP}-a^*_{BN})^2+(b^*_{BP}-b^*_{BN})^2]^{1/2}$

| Composition | Hair type | L* | a* | b* | ΔE |
|---|---|---|---|---|---|
| D (invention) | Before shampoo | 49.62 | 19.52 | 25.22 | 1.82 |
| | After shampoo | 51.41 | 19.66 | 25.54 | |
| E | Before shampoo | 53.08 | 16.91 | 24.39 | 21.29 |
| | After shampoo | 65 | 2.13 | 14.77 | |

Composition D presents a lower ΔE value than composition E: the persistence of the coloured coating toward shampoo is better with composition D than with comparative composition E.

The invention claimed is:
1. A method for dyeing keratin fibers, comprising:
 applying to the keratin fibers a composition comprising:
  at least one aqueous dispersion of particles of at least one hybrid film-forming hydrophobic acrylic polymer, at least one linear block silicone copolymer obtained by a chain extension reaction from:
a) at least one polysiloxane (i) having at least one reactive group per molecule; and
b) at least one organosilicone compound (ii) which reacts with the polysiloxane (i) by a chain extension reaction, and
at least one pigment, and
optionally drying the keratin fibers.

2. The method according to claim 1, wherein the at least one linear block silicone copolymer is in the form of particles in dispersion in an aqueous medium.

3. The method according to claim 1, wherein the polysiloxane (i) is chosen from the compounds of formula (I):

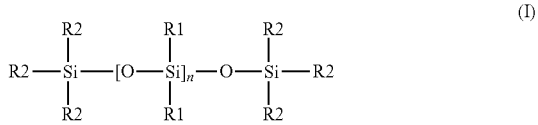

wherein:
R1 and R2 are independently chosen from hydrocarbon groups comprising from 1 to 20 carbon atoms, aryl groups, and reactive groups, and
n is an integer greater than 1,
with the proviso that there are on average between one and two reactive groups per polymer.

4. The method according to claim 3, where the reactive groups are chosen from hydrogen, aliphatically unsaturated groups, hydroxyl, alkoxy groups, alkoxy-alkoxy groups, acetoxy, amino groups, or mixtures thereof.

5. The method according to claim 3, wherein Rt is a methyl group and R2 at the chain end is a vinyl group.

6. The method according to claim 1, wherein the organosilicone compound (ii) is chosen from polysiloxanes of formula (I) and chain-extending agents.

7. The method according to claim 6, wherein the chain-extending agents are chosen from silanes, siloxanes, and silazanes.

8. The method according to claim 1, wherein the organosilicone compound (ii) is chosen from liquid organohydropolysiloxanes of formula (II):

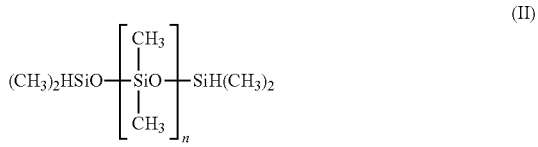

wherein n is an integer greater than 1.

9. The method according to claim 8, wherein n is an integer greater than 10.

10. The method according to claim 2, wherein the aqueous dispersion of particles of linear block silicone copolymer is obtained by mixing water, at least one emulsifier, at least one polysiloxane (i), at least one organosilicone compound (ii), and at least one catalyst.

11. The method according to claim 2, wherein the aqueous dispersion of particles of linear block silicone copolymer is an aqueous dispersion of divinyldimethicone/dimethicone copolymer.

12. The method according to claim 1, wherein the at least one linear block silicone copolymer is present in the composition in an amount, as polymeric active materials, ranging from about 0.1% to about 30% by weight, relative to the total weight of the composition.

13. The method according to claim 1, wherein the at least one hybrid film-forming hydrophobic acrylic polymer is synthesized from at least one monomer having at least one (meth)acrylic acid group and/or from esters of these acid monomers and/or from amides of these acid monomers, and from at least one styrene compound.

14. The method according to claim 1, wherein the at least one hybrid film-forming hydrophobic acrylic polymer is chosen from styrene/acrylate copolymers resulting from the polymerization of at least one styrene monomer and of at least one C1-C10 alkyl acrylate monomer.

15. The method according to claim 1, wherein the at least one aqueous dispersion of particles of at least one hybrid film-forming hydrophobic acrylic polymer is present in the composition in an amount, as polymeric active materials, ranging from about 0.1% to about 30% by weight, relative to the total weight of the composition.

16. The method according to claim 1, wherein the at least one hybrid film-forming hydrophobic acrylic polymer and the at least one linear block silicone copolymer are present in the composition in a weight ratio ranging from about 0.2 to about 10.

17. The method according to claim 1, wherein the at least one pigment is present in the composition in an amount ranging from about 0.01% to about 30% by weight, relative to the total weight of the composition.

18. The method according to claim 1, wherein the composition further comprises at least one inorganic thickening agent chosen from clays.

19. A method of dyeing keratin fibers comprising applying to the keratin fibers a dyeing composition comprising:
from 1% to 15% of styrene/acrylates copolymer;
from 1% to 15% of divinyldimethicone/dimethicone copolymer;
at least one pigment;
at least one thickener; and
water,
wherein all percentages are amounts of active material by weight, relative to the total weight of the dyeing composition.

20. The method of claim 19, wherein the keratin fibers are dried at a temperature ranging from 45° C. to 220° C. after the dyeing composition has been applied.

* * * * *

UNITED STATES PATENT AND TRADEMARK OFFICE
CERTIFICATE OF CORRECTION

PATENT NO. : 12,151,013 B2
APPLICATION NO. : 17/389917
DATED : November 26, 2024
INVENTOR(S) : Karen Teboul Page 1 of 1

It is certified that error appears in the above-identified patent and that said Letters Patent is hereby corrected as shown below:

In the Claims

Claim 5, Column 21, Line 34, please change 'Rt' to -- R1 --.

Signed and Sealed this
Twenty-fifth Day of March, 2025

Coke Morgan Stewart
*Acting Director of the United States Patent and Trademark Office*